(12) United States Patent
Woloszko et al.

(10) Patent No.: US 9,649,148 B2
(45) Date of Patent: May 16, 2017

(54) ELECTROSURGICAL SYSTEM AND METHOD HAVING ENHANCED ARC PREVENTION

(71) Applicant: ArthroCare Corporation, Austin, TX (US)

(72) Inventors: Jean Woloszko, Austin, TX (US); Jonathan L. Gaspredes, Austin, TX (US); Scott A. Armstrong, Wimberley, TX (US)

(73) Assignee: ArthroCare Corporation, Austin, TX (US)

( * ) Notice: Subject to any disclaimer, the term of this patent is extended or adjusted under 35 U.S.C. 154(b) by 309 days.

(21) Appl. No.: 14/339,583

(22) Filed: Jul. 24, 2014

(65) Prior Publication Data
US 2016/0022349 A1    Jan. 28, 2016

(51) Int. Cl.
*A61B 18/14* (2006.01)
*A61B 18/12* (2006.01)
(Continued)

(52) U.S. Cl.
CPC ........ *A61B 18/1233* (2013.01); *A61B 18/042* (2013.01); *A61B 18/1206* (2013.01);
(Continued)

(58) Field of Classification Search
CPC ... A61B 18/1233; A61B 18/042; A61B 18/14; A61B 18/1206; A61B 2018/0072;
(Continued)

(56) References Cited

U.S. PATENT DOCUMENTS

| 2,050,904 A | 8/1936 | Trice ............................. 219/233 |
| 2,275,167 A | 3/1942 | Bierman ......................... 606/50 |

(Continued)

FOREIGN PATENT DOCUMENTS

| DE | 2521719 | 11/1976 | ............... A61N 3/02 |
| DE | 4425015 | 1/1996 | ............. A61B 17/36 |

(Continued)

OTHER PUBLICATIONS

Buchelt, et al. "Excimer Laser Ablation of Fibrocartilage: An In Vitro and In Vivo Study", Lasers in Surgery and Medicine, vol. 11, pp. 271-279, 1991.

(Continued)

*Primary Examiner* — Michael Peffley
(74) *Attorney, Agent, or Firm* — David A. Warmbold

(57) ABSTRACT

Electrosurgical systems and methods are described herein, the system including an electrosurgical probe with an active electrode disposed near the probe distal end, a system with a power supply for delivery of voltage to the active electrode and a controller that receives and processes a signal from a current sensor and a temperature sensor. The current sensor measures the current output of the power supply and the temperature sensor is adjacent an electrically conductive fluid located at a target site. The controller may be programmed to operate in a low voltage mode that limits the power supply to a low voltage output so as to determine whether the current output from the current sensor is within a current output range. This range is defined by predetermined upper and lower limits that are modified by at least one measured value.

28 Claims, 7 Drawing Sheets

(51) Int. Cl.
  *A61B 18/04* (2006.01)
  *A61B 18/00* (2006.01)
(52) U.S. Cl.
  CPC ...... *A61B 18/14* (2013.01); *A61B 2018/0072* (2013.01); *A61B 2018/00678* (2013.01); *A61B 2018/00767* (2013.01); *A61B 2018/00779* (2013.01); *A61B 2018/00791* (2013.01); *A61B 2018/00827* (2013.01); *A61B 2018/00875* (2013.01); *A61B 2018/00892* (2013.01)
(58) Field of Classification Search
  CPC  A61B 2018/00892; A61B 2018/00767; A61B 2018/00827; A61B 2018/00678; A61B 2018/00791; A61B 2018/00875; A61B 2018/00779
  See application file for complete search history.

(56) References Cited

U.S. PATENT DOCUMENTS

| | | | |
|---|---|---|---|
| 3,699,967 A | 10/1972 | Anderson | 606/37 |
| 3,812,858 A | 5/1974 | Oringer | 604/22 |
| 3,945,375 A | 3/1976 | Banko | 600/104 |
| 4,033,351 A | 7/1977 | Hetzel | 606/48 |
| 4,203,444 A | 5/1980 | Bonnell et al. | 604/22 |
| 4,240,441 A | 12/1980 | Khalil | 128/692 |
| 4,269,174 A | 5/1981 | Adair | 128/842 |
| 4,411,266 A | 10/1983 | Cosman | 606/49 |
| 4,429,694 A | 2/1984 | McGreevy | 128/303.14 |
| 4,483,338 A | 11/1984 | Bloom et al. | 606/50 |
| 4,582,057 A | 4/1986 | Auth et al. | 606/31 |
| 4,641,649 A | 2/1987 | Walinsky | 606/33 |
| 4,674,499 A | 6/1987 | Pao | 606/50 |
| 4,709,698 A | 12/1987 | Johnston et al. | 128/303 |
| 4,719,914 A | 1/1988 | Johnson | 606/28 |
| 4,736,743 A | 4/1988 | Diakuzono | 128/303.1 |
| 4,737,678 A | 4/1988 | Hasegawa | 313/36 |
| 4,762,128 A | 8/1988 | Rosenbluth | 128/343 |
| 4,785,806 A | 11/1988 | Deckelbaum | 128/303.1 |
| 4,813,429 A | 3/1989 | Eshel et al. | 128/736 |
| 4,827,911 A | 5/1989 | Broadwin et al. | 604/22 |
| 4,860,752 A | 8/1989 | Turner et al. | 128/422 |
| 4,903,696 A | 2/1990 | Stasz et al. | 606/37 |
| 4,940,064 A | 7/1990 | Desai | 607/122 |
| 4,955,377 A | 9/1990 | Lennox et al. | 128/401 |
| 4,968,314 A | 11/1990 | Michaels | 606/7 |
| 4,976,709 A | 12/1990 | Sand | 606/5 |
| 5,007,437 A | 4/1991 | Sterzer | 428/786 |
| 5,037,421 A | 8/1991 | Boutacoff et al. | 606/15 |
| 5,057,105 A | 10/1991 | Malone et al. | 606/28 |
| 5,057,106 A | 10/1991 | Kasevich et al. | 606/33 |
| 5,061,266 A | 10/1991 | Hakky | 606/15 |
| 5,083,565 A | 1/1992 | Parins | 128/642 |
| 5,084,045 A | 1/1992 | Helenowski | 606/32 |
| 5,092,339 A | 3/1992 | Geddes et al. | 128/692 |
| 5,093,877 A | 3/1992 | Aita et al. | 385/34 |
| 5,103,804 A | 4/1992 | Abele et al. | 600/116 |
| 5,137,530 A | 8/1992 | Sand | 606/5 |
| 5,147,354 A | 9/1992 | Boutacoff et al. | 606/15 |
| 5,151,098 A | 9/1992 | Loertscher | 606/16 |
| 5,176,528 A | 1/1993 | Fry et al. | 439/181 |
| 5,191,883 A | 3/1993 | Lennox et al. | 607/102 |
| 5,217,455 A | 6/1993 | Tan | 606/9 |
| 5,230,334 A | 7/1993 | Klopotek | 601/3 |
| 5,234,428 A | 8/1993 | Kaufman | 606/45 |
| 5,246,438 A | 9/1993 | Langberg | 606/33 |
| 5,249,585 A | 10/1993 | Turner et al. | 607/99 |
| 5,269,794 A | 12/1993 | Rexroth | 606/180 |
| 5,277,696 A | 1/1994 | Hagen | 606/49 |
| 5,293,868 A | 3/1994 | Nardella | 600/373 |
| 5,295,956 A | 3/1994 | Bales et al. | 604/30 |
| 5,300,099 A | 4/1994 | Rudie | 607/101 |
| 5,301,687 A | 4/1994 | Wong et al. | 607/116 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,318,563 A | 6/1994 | Malis et al. | 606/38 |
| 5,322,507 A | 6/1994 | Costello et al. | 128/4 |
| 5,330,518 A | 7/1994 | Neilson et al. | 607/101 |
| 5,334,183 A | 8/1994 | Wuchinich | 606/46 |
| 5,334,193 A | 8/1994 | Nardella | 606/41 |
| 5,335,668 A | 8/1994 | Nardella | 600/547 |
| 5,336,217 A | 8/1994 | Buys et al. | 606/9 |
| 5,336,220 A | 8/1994 | Ryan et al. | 604/22 |
| 5,348,554 A | 9/1994 | Imran et al. | 606/41 |
| 5,370,642 A | 12/1994 | Keller | 606/9 |
| 5,370,644 A | 12/1994 | Langberg | 606/33 |
| 5,374,265 A | 12/1994 | Sand | 606/5 |
| 5,395,363 A | 3/1995 | Billings et al. | 606/41 |
| 5,403,311 A | 4/1995 | Abele et al. | 606/49 |
| 5,405,376 A | 4/1995 | Mulier et al. | 607/127 |
| 5,423,803 A | 6/1995 | Tankovich | 606/9 |
| 5,423,844 A | 6/1995 | Miller | 606/171 |
| 5,431,649 A | 7/1995 | Mulier et al. | 606/41 |
| 5,433,708 A | 7/1995 | Nichols et al. | 604/113 |
| 5,437,664 A | 8/1995 | Cohen et al. | 606/42 |
| 5,445,634 A | 8/1995 | Keller | 606/9 |
| 5,458,596 A | 10/1995 | Lax et al. | 606/31 |
| 5,462,545 A | 10/1995 | Wang et al. | 606/41 |
| 5,484,435 A | 1/1996 | Fleenor et al. | 606/46 |
| 5,487,385 A | 1/1996 | Avitall | 600/374 |
| 5,490,850 A | 2/1996 | Ellman et al. | 606/45 |
| 5,505,710 A | 4/1996 | Dorsey, III | 604/158 |
| 5,520,685 A | 5/1996 | Wojciechowicz | 606/49 |
| 5,536,267 A | 7/1996 | Edwards et al. | 606/41 |
| 5,542,928 A | 8/1996 | Evans et al. | 604/113 |
| 5,545,161 A | 8/1996 | Imran | 606/41 |
| 5,562,703 A | 10/1996 | Desai | 606/210 |
| 5,579,764 A | 12/1996 | Goldreyer | 600/374 |
| 5,607,391 A | 3/1997 | Klinger et al. | 604/33 |
| 5,607,421 A | 3/1997 | Jeevanandam et al. | 606/15 |
| 5,626,576 A | 5/1997 | Janssen | 606/41 |
| 5,643,255 A | 7/1997 | Organ | 606/41 |
| 5,653,692 A | 8/1997 | Masterson et al. | 604/113 |
| 5,660,836 A | 8/1997 | Knowlton | 607/101 |
| 5,681,308 A | 10/1997 | Edwards et al. | 606/41 |
| 5,688,267 A | 11/1997 | Panescu et al. | 606/41 |
| 5,713,896 A | 2/1998 | Nardella | 606/50 |
| 5,743,870 A | 4/1998 | Edwards | 604/22 |
| 5,743,903 A | 4/1998 | Stern et al. | 606/31 |
| 5,746,746 A | 5/1998 | Garito et al. | 606/41 |
| 5,749,869 A | 5/1998 | Lindenmeier et al. | 606/34 |
| 5,755,753 A | 5/1998 | Knowlton | 607/98 |
| 5,769,843 A | 6/1998 | Abela et al. | 606/10 |
| 5,769,847 A | 6/1998 | Panescu et al. | 606/42 |
| 5,772,659 A * | 6/1998 | Becker | A61B 18/1206 322/7 |
| 5,782,795 A | 7/1998 | Bays | 604/22 |
| 5,785,705 A | 7/1998 | Baker | 606/32 |
| 5,800,429 A | 9/1998 | Edwards | 606/41 |
| 5,800,431 A | 9/1998 | Brown | 606/42 |
| 5,807,384 A | 9/1998 | Mueller | 606/7 |
| 5,810,802 A | 9/1998 | Panescu et al. | 606/31 |
| 5,843,078 A | 12/1998 | Sharkey | 606/41 |
| 5,855,277 A | 1/1999 | Apps et al. | 606/35 |
| 5,871,524 A | 2/1999 | Knowlton | 607/101 |
| 5,876,398 A | 3/1999 | Mulier et al. | 606/41 |
| 5,893,848 A | 4/1999 | Negus et al. | 606/41 |
| 5,895,386 A | 4/1999 | Odell et al. | 606/50 |
| 5,904,681 A | 5/1999 | West, Jr. | 606/41 |
| 5,906,613 A | 5/1999 | Mulier et al. | 606/41 |
| 5,919,219 A | 7/1999 | Knowlton | 607/102 |
| 5,964,754 A | 10/1999 | Osypka | 606/37 |
| 5,976,127 A | 11/1999 | Lax | 606/32 |
| 5,980,516 A | 11/1999 | Mulier et al. | 606/41 |
| 5,980,545 A | 11/1999 | Pacala et al. | 606/170 |
| 5,984,919 A | 11/1999 | Hilal et al. | 606/45 |
| 6,007,533 A | 12/1999 | Casscells et al. | 606/45 |
| 6,007,570 A | 12/1999 | Sharkey et al. | 607/96 |
| 6,016,809 A | 1/2000 | Mulier et al. | 128/898 |
| 6,030,383 A | 2/2000 | Benderev | 606/45 |
| 6,032,673 A | 3/2000 | Savage et al. | 128/898 |
| 6,032,674 A | 3/2000 | Eggers et al. | 606/41 |

(56) References Cited

U.S. PATENT DOCUMENTS

| | | | |
|---|---|---|---|
| 6,042,580 A | 3/2000 | Simpson | 606/32 |
| 6,045,532 A | 4/2000 | Eggers et al. | 604/114 |
| 6,053,172 A | 4/2000 | Hovda et al. | 128/898 |
| 6,063,081 A | 5/2000 | Mulier et al. | 606/45 |
| 6,091,995 A | 7/2000 | Ingle et al. | 607/138 |
| 6,096,037 A | 8/2000 | Mulier et al. | 606/49 |
| 6,110,169 A | 8/2000 | Mueller et al. | 606/48 |
| 6,142,992 A * | 11/2000 | Cheng | A61B 18/1206 606/34 |
| 6,152,923 A | 11/2000 | Ryan | 606/51 |
| 6,156,031 A | 12/2000 | Aita et al. | 606/33 |
| 6,210,405 B1 | 4/2001 | Gobel et al. | 606/41 |
| 6,214,001 B1 | 4/2001 | Casscells et al. | 606/41 |
| 6,217,575 B1 | 4/2001 | DeVore et al. | 606/41 |
| 6,235,023 B1 | 5/2001 | Lee et al. | 606/41 |
| 6,238,393 B1 | 5/2001 | Mulier et al. | 607/127 |
| 6,264,650 B1 | 7/2001 | Hovda | 606/32 |
| 6,267,757 B1 | 7/2001 | Aita et al. | 606/33 |
| 6,283,961 B1 | 9/2001 | Underwood et al. | 606/41 |
| 6,302,903 B1 | 10/2001 | Mulier et al. | 607/105 |
| 6,312,429 B1 | 11/2001 | Butbank et al. | 606/47 |
| 6,315,774 B1 | 11/2001 | Daniel et al. | 606/15 |
| 6,322,494 B1 | 11/2001 | Bullivant et al. | 600/104 |
| 6,325,799 B1 | 12/2001 | Goble | 606/41 |
| 6,327,505 B1 | 12/2001 | Medhkour et al. | 607/99 |
| 6,328,736 B1 | 12/2001 | Mulier et al. | 606/45 |
| 6,336,926 B1 | 1/2002 | Goble | 606/34 |
| 6,346,107 B1 | 2/2002 | Cucin | 606/49 |
| 6,355,006 B1 | 3/2002 | Ryaby et al. | 601/2 |
| 6,358,248 B1 | 3/2002 | Mulier et al. | 606/41 |
| 6,379,350 B1 | 4/2002 | Sharkey et al. | 606/41 |
| 6,391,028 B1 | 5/2002 | Fanton et al. | 606/45 |
| 6,398,781 B1 | 6/2002 | Gobel et al. | 606/41 |
| 6,409,724 B1 | 6/2002 | Penny et al. | 606/41 |
| 6,432,105 B1 | 8/2002 | Ellman et al. | 606/48 |
| 6,482,202 B1 | 11/2002 | Goble et al. | 606/41 |
| 6,491,690 B1 | 12/2002 | Gobel et al. | 606/41 |
| 6,497,705 B2 | 12/2002 | Comben | 606/41 |
| 6,497,706 B1 | 12/2002 | Burbank et al. | 606/45 |
| 6,510,854 B2 | 1/2003 | Gobel | 128/898 |
| 6,514,250 B1 | 2/2003 | Jahns et al. | 606/41 |
| 6,517,535 B2 | 2/2003 | Edwards | 606/41 |
| 6,540,741 B1 | 4/2003 | Underwood et al. | 606/32 |
| 6,557,559 B1 | 5/2003 | Eggers et al. | 128/898 |
| 6,575,968 B1 | 6/2003 | Eggers et al. | 606/41 |
| 6,575,969 B1 | 6/2003 | Rittman, III et al. | 606/41 |
| 6,582,423 B1 | 6/2003 | Thapliyal et al. | 606/32 |
| 6,595,990 B1 | 7/2003 | Weinstein et al. | 606/41 |
| 6,597,950 B2 | 7/2003 | Linder et al. | 607/8 |
| 6,605,085 B1 | 8/2003 | Edwards | 606/41 |
| 6,610,059 B1 | 8/2003 | West, Jr. | 606/41 |
| 6,632,230 B2 | 10/2003 | Barry | 606/159 |
| 6,645,203 B2 | 11/2003 | Sharkey et al. | 606/41 |
| 6,663,628 B2 | 12/2003 | Peters | 606/45 |
| 6,695,839 B2 | 2/2004 | Sharkey et al. | 606/41 |
| 6,699,206 B2 | 3/2004 | Burbank et al. | 606/567 |
| 6,699,244 B2 | 3/2004 | Carranza et al. | 606/41 |
| 6,702,810 B2 | 3/2004 | McClurken et al. | 606/34 |
| 6,746,447 B2 | 6/2004 | Davison et al. | 606/41 |
| 6,763,836 B2 | 7/2004 | Tasto et al. | 128/898 |
| 6,796,981 B2 * | 9/2004 | Wham | A61B 18/1445 606/34 |
| 6,796,982 B2 | 9/2004 | Carmel et al. | 606/41 |
| 6,805,130 B2 | 10/2004 | Tasto et al. | 606/32 |
| 6,827,725 B2 | 12/2004 | Batchelor et al. | 606/170 |
| 6,832,996 B2 | 12/2004 | Woloszko et al. | 606/41 |
| 6,855,143 B2 | 2/2005 | Davison et al. | 606/41 |
| 6,896,674 B1 | 5/2005 | Woloszko et al. | 606/41 |
| 6,904,303 B2 | 6/2005 | Phan et al. | 600/374 |
| 6,979,332 B2 | 12/2005 | Adams | 606/45 |
| 7,137,980 B2 * | 11/2006 | Buysse | A61B 18/1206 606/34 |
| 7,150,747 B1 | 12/2006 | McDonald et al. | 606/45 |
| 7,184,811 B2 | 2/2007 | Phan et al. | 600/374 |
| 7,261,571 B2 | 8/2007 | Chen et al. | 606/45 |
| 7,261,712 B2 | 8/2007 | Burbank et al. | 606/49 |
| 7,364,577 B2 * | 4/2008 | Wham | A61B 18/00 606/34 |
| 7,429,262 B2 | 9/2008 | Woloszko et al. | 606/48 |
| 7,488,295 B2 | 2/2009 | Burbank et al. | 606/167 |
| 7,776,034 B2 | 8/2010 | Kampa | 606/41 |
| 7,819,863 B2 | 10/2010 | Eggers et al. | 606/32 |
| 8,038,670 B2 | 10/2011 | McClurken | 606/41 |
| 8,317,786 B2 | 11/2012 | Dahla et al. | 606/48 |
| 8,323,279 B2 | 12/2012 | Dahla et al. | 606/48 |
| 8,355,799 B2 | 1/2013 | Marion et al. | 607/102 |
| 8,747,400 B2 | 6/2014 | Bigley et al. | 606/41 |
| 2002/0032439 A1 | 3/2002 | Hareyama | |
| 2002/0049438 A1 | 4/2002 | Sharkey et al. | 606/41 |
| 2002/0072739 A1 | 6/2002 | Lee et al. | 606/47 |
| 2003/0036753 A1 | 2/2003 | Morgan et al. | 606/32 |
| 2003/0097129 A1 | 5/2003 | Davison et al. | 606/41 |
| 2003/0130711 A1 | 7/2003 | Pearson et al. | 607/101 |
| 2004/0030330 A1 | 2/2004 | Brassell et al. | 606/41 |
| 2007/0149965 A1 | 6/2007 | Gallo et al. | 606/41 |
| 2008/0021447 A1 | 1/2008 | Davison et al. | 606/41 |
| 2008/0167645 A1 | 7/2008 | Woloszko | 606/40 |
| 2008/0167646 A1 | 7/2008 | Godara et al. | 606/41 |
| 2008/0234673 A1 | 9/2008 | Marion et al. | 606/45 |
| 2008/0300590 A1 | 12/2008 | Horne et al. | 606/35 |
| 2009/0138011 A1 | 5/2009 | Epstein | 606/42 |
| 2009/0209958 A1 | 8/2009 | Davison et al. | 606/41 |
| 2010/0042095 A1 | 2/2010 | Bigley et al. | 606/41 |
| 2010/0204690 A1 | 8/2010 | Bigley et al. | 606/41 |
| 2011/0270242 A1 * | 11/2011 | Marion | A61B 18/148 606/35 |
| 2012/0179157 A1 | 7/2012 | Frazier et al. | 606/41 |
| 2012/0215213 A1 | 8/2012 | Juzkiw et al. | |
| 2013/0096556 A1 * | 4/2013 | Lorang | A61B 18/1206 606/42 |
| 2013/0116689 A1 | 5/2013 | Marion | 606/42 |
| 2014/0155883 A1 | 6/2014 | Marion | 606/34 |
| 2014/0155884 A1 | 6/2014 | Marion | 606/35 |

FOREIGN PATENT DOCUMENTS

| | | | |
|---|---|---|---|
| DE | 296 09 350 | 8/1996 | A61B 17/39 |
| DE | 195 37 084 | 4/1997 | A61B 17/36 |
| DE | 296 19 029 | 4/1997 | A61B 17/34 |
| DE | 19850671 | 5/1999 | A61B 17/22 |
| DE | 10254668 | 6/2004 | A61B 18/12 |
| DE | 69822877 | 1/2005 | A61B 17/20 |
| DE | 202008000276 | 6/2008 | A61B 18/12 |
| DE | 102009057921 A1 | 6/2010 | A61B 18/12 |
| EP | 0 502 268 | 9/1992 | A61B 17/39 |
| EP | 0 515 867 | 12/1992 | A61B 17/36 |
| EP | 543123 | 5/1993 | A61B 17/39 |
| EP | 0 597 463 | 5/1994 | A61N 5/04 |
| EP | 774926 | 3/1995 | A61B 17/39 |
| EP | 0 650 701 | 5/1995 | A61B 17/39 |
| EP | 923907 | 6/1999 | A61B 17/39 |
| EP | 1149564 | 10/2001 | A61B 18/14 |
| EP | 1041933 | 3/2004 | A61B 17/20 |
| GB | 2037167 | 7/1980 | A61B 17/36 |
| GB | 2331247 | 5/1999 | A61B 17/39 |
| GB | 2379878 | 3/2003 | A61B 18/04 |
| GB | 2408936 | 6/2005 | A61B 18/14 |
| JP | 57-183850 | 11/1982 | A61F 9/00 |
| JP | 63-40099 | 8/1988 | A61B 17/39 |
| JP | 9-501328 | 2/1997 | A61B 17/39 |
| WO | 91/13650 | 9/1991 | A61N 5/04 |
| WO | 94/03134 | 2/1994 | A61B 18/20 |
| WO | 94/10924 | 5/1994 | A61B 17/39 |
| WO | 94/14383 | 7/1994 | A61B 17/36 |
| WO | 94/26228 | 11/1994 | A61G 17/36 |
| WO | 95/05780 | 3/1995 | A61B 17/36 |
| WO | 95/05781 | 3/1995 | A61B 17/39 |
| WO | 95/05867 | 3/1995 | A61N 1/05 |
| WO | 95/10326 | 4/1995 | A61N 5/00 |
| WO | 95/30373 | 11/1995 | A61B 17/00 |
| WO | 9604860 | 2/1996 | |
| WO | 96/07360 | 3/1996 | A61B 17/39 |
| WO | 96/34568 | 11/1996 | A61B 17/36 |
| WO | 96/35469 | 11/1996 | A61B 17/36 |

(56) References Cited

FOREIGN PATENT DOCUMENTS

| | | | |
|---|---|---|---|
| WO | 96/39914 | 12/1996 | ............ A61B 1/00 |
| WO | 96/39962 | 12/1996 | ............ A61B 17/36 |
| WO | 96/39964 | 12/1996 | ............ A61B 17/36 |
| WO | 96/39965 | 12/1996 | ............ A61B 17/36 |
| WO | 96/39967 | 12/1996 | ............ A61B 17/38 |
| WO | 97/15238 | 5/1997 | ............ A61B 17/39 |
| WO | 97/18765 | 5/1997 | ............ A61B 17/36 |
| WO | 97/24992 | 7/1997 | ............ A61B 17/38 |
| WO | 97/25101 | 7/1997 | ............ A61N 5/00 |
| WO | 97/32551 | 9/1997 | ............ A61F 11/00 |
| WO | 97/33523 | 9/1997 | ............ A61B 17/32 |
| WO | 97/34540 | 9/1997 | ............ A61B 17/36 |
| WO | 97/41786 | 11/1997 | ............ A61B 17/39 |
| WO | 97/44071 | 11/1997 | ............ A61M 1/10 |
| WO | 9803117 | 1/1998 | |
| WO | 98/14131 | 4/1998 | ............ A61B 18/14 |
| WO | 98/17185 | 4/1998 | ............ A61B 17/36 |
| WO | 98/17186 | 4/1998 | ............ A61B 17/36 |
| WO | 98/27877 | 7/1998 | ............ A61B 17/32 |
| WO | 98/30144 | 7/1998 | ............ A61B 17/36 |
| WO | 98/34550 | 8/1998 | ............ A61B 17/39 |
| WO | 98/34558 | 8/1998 | ............ A61B 18/00 |
| WO | 98/38925 | 9/1998 | ............ A61B 17/20 |
| WO | 98/39038 | 9/1998 | ............ A61M 5/00 |
| WO | 99/00060 | 1/1999 | ............ A61B 17/22 |
| WO | 99/20185 | 4/1999 | ............ A61B 17/20 |
| WO | 99/42037 | 8/1999 | ............ A61B 17/00 |
| WO | 99/44506 | 9/1999 | ............ A61B 10/00 |
| WO | 00/09053 | 2/2000 | ............ A61F 7/12 |
| WO | 01/26570 | 4/2001 | ............ A61B 18/14 |
| WO | 01/95819 | 12/2001 | ............ A61B 18/14 |
| WO | 02/078557 | 10/2002 | ............ A61B 18/18 |
| WO | 03/024339 | 3/2003 | ............ A61B 17/32 |
| WO | 2008/073727 | 6/2008 | ............ A61B 18/14 |
| WO | 2009/094392 | 7/2009 | ............ A61B 18/14 |
| WO | 2011/071482 | 6/2011 | ............ A61B 18/14 |

OTHER PUBLICATIONS

Costello et al., "Nd: YAG Laser Ablation of the Prostate as a Treatment for Benign Prostatic Hypertrophy", Lasers in Surgery and Medicine, vol. 12, pp. 121-124, 1992.
Hardy et al., "Regional Myocardial Blood Flow and Cardiac mechanics in dog Hearts with CO2 laser-induced Intramyocardial Revascularization", Basic Research in cardiology 85:179-196 (1990).
Mirhoseini et al., "New Concepts in Revascularization of the Myocardium", Ann Thorac Surg 45:415-420 (1988).
Mirhoseini et al., "Revascularization of the heart by Laser", J. of Microsurgery 2:253-260 (1981).
Mirhoseini et al., "Transmyocardial Laser Revascularization: A Review", J. of Clinical Laser medicine & Surgery 11 (1) :15-19 (1993).
Mirhoseini et al., "Transventricular Revascularization by Laser", Lasers in Surgery and Medicine 2:187-198 (1982).
Rand et al., "Effect of Elecctrocautery on Fresh Human Articular Cartilage", J. Arthro. Surg., vol. 1, pp. 242-246, 1985.
Walter et al., "Treatment of Acute Mycardial Infarction by Transmural Blood Supply from the Ventricular Cavity", Erop. Surgery Res. 3:130-138 (1971).
Whittaker et al., "Transmural Channels Can Protect Ischemic Tissue", Circulation 93(1):143-152 Jan. 1, 1996.
EP Search Report for EP01124768 2 pgs Nov. 30, 2001.
EP Search Report for EP01935650 10 pgs Mailed Jul. 26, 2006.
EP Search Report for EP01935650 8 pgs Mailed May 3, 2005.
EP Search Report for EP02768969 3 pgs Mailed Feb. 12, 2007.
EP Search Report for EP03762238 3 pgs Mailed Jun. 2, 2006.
EP Search Report for EP94916716 2 pgs Oct. 29, 1996.
EP Search Report for EP96941386 2 pgs Nov. 27, 1998.
EP Search Report for EP98952032 2 pgs Nov. 24, 2000.
EP Search Report for EP 03736488 3 pgs Mailed Jun. 25, 2009.
EP Search Report for EP 07118068 3pgs Mailed Dec. 27, 2010.
EP Search Report for EP 04778347 4pgs Feb. 22, 2011.
PCT International Search Report for PCT/US00/07718 1 pg Mailed Sep. 5, 2000.
PCT International Search Report for PCT/US01/16006 1pg Mailed Aug. 14, 2001.
PCT International Search Report for PCT/US02/31640 1pg Mailed May 23, 2003.
PCT International Search Report for PCT/US03/04689 1pg Mailed Sep. 26, 2003.
PCT International Search Report for PCT/US03/12790 1pg Mailed Aug. 12, 2003.
PCT International Search Report for PCT/US03/20574 1pg Mailed May 25, 2005.
PCT International Search Report for PCT/US04/22803 1pg Mailed Apr. 29, 2005.
PCT International Search Report for PCT/US05/07038 1pg Mailed Sep. 2, 2005.
PCT International Search Report for PCT/US94/05168, 1 pg Mailed Oct. 18, 1994.
PCT International Search Report for PCT/US96/18505, 3 pgs Mailed Jan. 17, 1997.
PCT International Search Report for PCT/US98/20768 1pg Mailed Jan. 20, 1999.
PCT International Search Report for PCT/US98/22327 1pg Mailed Feb. 9, 1999.
PCT Notif of the Int'l Search Report and Written Opinion for PCT/US09/67001 6 pgs; Mailed Jan. 29, 2010.
PCT IPER for PCT/US01/16006 3pgs Apr. 16, 2002.
PCT IPER for PCT/US98/22327 4pgs Aug. 27, 2000.
PCT Written Opinion for PCT/US04/22803 3pgs Mailed Apr. 29, 2005.
PCT Written Opinion for PCT/US05/07038 3pgs Mailed Sep. 2, 2005.
UK Search Report for GB0805061.9 1 pg Jul. 15, 2008.
UK Search Report for GB0921635.9 3pgs Apr. 12, 2010.
K Search Report for GB1106425.0 6 pages, Aug. 16, 2011.
UK combined Search and Examination Report for GB1121048.1 3pgs, Apr. 18, 2012.
IPRP for PCT/US2015/037196 dated Feb. 2, 2017, 10 pages.

* cited by examiner

ELECTROSURGICAL SYSTEM AND METHOD HAVING ENHANCED ARC PREVENTION

FIELD OF THE INVENTION

The present invention relates to systems and methods for detecting and preventing non-optimal conditions or faults during electrosurgical procedures within a body space of a patient body, such as within a joint. More particularly, the present invention relates to methods and apparatus for utilizing a combination of both electrical measurements at low voltages and at least one other measureable to better evaluate conditions within a body space before or between electrosurgical treatments of tissue.

RELATED REFERENCES

The present invention is related to commonly assigned U.S. Pat. No. 6,142,992, filed Apr. 10, 1998, U.S. Pat. No. 6,235,020, filed Apr. 10, 1998, entitled "Power Supply and Methods for Fluid Delivery in Electrosurgery", U.S. patent application Ser. No. 12/771,129, filed on Apr. 30, 2010 entitled "Electrosurgical Systems and Method having Enhanced Temperature Measurement", and U.S. patent application Ser. No. 14/192,978, filed Feb. 28, 2014 entitled "Systems and Methods Systems related to Electrosurgical Wands with Screen Electrodes" the complete disclosures of which are herein incorporated by reference.

BACKGROUND OF THE INVENTION

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of RF current that is placed away from the surgical site on the body of the patient, and where the surgical device defines only a single electrode pole that provides the surgical effect. Bipolar devices comprise both electrodes for the application of current between their surfaces.

Electrosurgical procedures and techniques are particularly advantageous as they generally reduce patient bleeding and trauma associated with cutting operations. Additionally, electrosurgical ablation procedures, where tissue surfaces and volume may be reshaped, is not easily duplicated through other treatment modalities.

Generally, radiofrequency (RF) energy is extensively used during arthroscopic procedures because it provides efficient tissue resection and coagulation and relatively easy access to the target tissues through a portal or cannula. Arthroscopic procedures, laproscopic procedures, and the like are often conducted in confined areas such as the synovial sac of the knee or similar body enclosures in the presence of a conductive medium such as an electrically conductive fluid (e.g., saline). However, a challenge with the surgical use of RF energy in confined spaces is that an electrode on the electrosurgical instrument is more likely to come into accidental contact or be placed in close proximity to a low impedance object, such as a metallic endoscope or a soft tissue implant or anchor. When an electrosurgical active electrode is placed in the proximity of metallic objects, there is a high concentration of the electrical field around the metal, and therefore the electrical field can easily exceed the medium, and generate an arc. Especially in cases when the electrical field created by the voltage exceeds the dielectric strength of this medium, an arc discharge plasma (or thermal plasma) may be formed with temperatures usually exceeding 1,500° C. when high frequency voltage is generated across the conductive medium. The high temperature generated by the arc, combined with the shock wave generated by the discharge plasma, can damage tissue, soft tissue implants, or other equipment like crystal lenses of an endoscope. Standard electrosurgical systems used in arthroscopic surgery or other types of surgery may have circuitry that detects high currents associated with arcs, and can be configured to interrupt the high frequency output very rapidly in order to mitigate any potential damage caused by the arc. However, in order to completely remove the risk of arcing and the resultant damage, the high currents associated with a potential arc needs to be dissipated before it is detected. Without such dissipation of the current, an arc may still form, even if only for a very short time (a few hundred nano seconds to several micro seconds, or even sometimes milliseconds) bring forth a potential risk of damaging the RF generator, the endoscope, the surrounding tissue, and any other adjacent tissue implant or surgical equipment.

Previous attempts to mitigate these damaging effects have included limiting the power output of the RF generator and measuring the current periodically to check for acceptable levels. These solutions may be effective to stop an arc once it has occurred but they do not predict or detect the possibility of an arc prior to the arc occurring. Furthermore, over-limiting the power output of the generator reduces the rate of the surgical effect, which is often unacceptable or an annoyance from a clinical perspective. An improved system and method to more accurately predict non-preferable conditions such as arcing to adjacent metallic instruments, accommodating for local temperatures and wear of the instrument is therefore desired.

SUMMARY

The present disclosure provides systems, apparatus and methods for minimizing the likelihood of an electrosurgical instrument arcing to a nearby metallic object, taking into account variables that may affect the possibility of arcing. These variables may include the instrument used and surgical procedure, as well as measureable variables, such as the temperature adjacent the instrument distal tip and wear of the distal tip and electrodes. The present disclosure also provides systems, apparatus and methods for indicating high impedance conditions at the distal end of the electrosurgical instrument using a low voltage.

In one aspect the present disclosure describes an electrosurgical system for treating tissue at a target site with an electrosurgical probe, the probe having a shaft with a distal end, a proximal end and an active electrode terminal disposed near the distal end. The system also includes a high frequency power supply for delivering high frequency voltage to the active electrode terminal. This high frequency power supply is coupled to both the active electrode terminal and a return electrode. The system may also include a controller that, amongst other things, receives and processes an output signal from a current sensor and a temperature sensor. The current sensor measures the current output of the power supply and the temperature sensor may be located in or near an electrically conductive fluid and is also located close to the target site. This electrically conductive fluid may provide a current path between the active electrode terminal and the return electrode. The controller is programmed to operate in a low voltage mode at times, that limits the power supply to a low voltage output until a current output from the current sensor is within an acceptable range. This range has a predetermined upper limit that may be modified by at least one measured value. In some embodiments this measured value is temperature and in some embodiments this temperature is measured at the temperature sensor.

In some embodiments the controller may automatically adjust the power supply to a higher voltage therapeutic mode once the current output is within the acceptable range. Additionally, the controller may also automatically return the power supply to the low voltage mode for at least one suspension period, should an arc be detected, and the suspension period may be repeated until the current output returns to within the acceptable range. In some embodiment the range upper limit increases as the measured temperature increases. In some embodiments the range has a predetermined lower limit that detects high impedance faults in the probe or insufficient electrically conductive fluid adjacent the active and return electrode.

In another aspect of the disclosure, a method of preventing arcing between an electrosurgical probe and a metallic object is disclosed, including the steps of delivering a low voltage high frequency energy from a high frequency power source to an active electrode terminal located at the distal end of the electrosurgical probe, followed by measuring a current output of the high frequency power source and a temperature output adjacent the active electrode. The predetermined high current limit may then be modified based on the temperature output and then the measured current output may be compared to this modified high current predetermined limit. In some embodiments high voltage high frequency therapeutic energy may then be delivered to the active electrode terminal if the current output is below the modified predetermined limit. In some embodiments the power source will continue to deliver the low voltage energy, should the current output continue to exceed the modified predetermined threshold limit. In some embodiments the power supply may automatically return to the steps of delivering low voltage energy should an arc be detected between the active electrode terminal and a metallic object while delivering high voltage therapeutic energy. In some embodiments the predetermined high current limit increases as the temperature increases.

DETAILED DESCRIPTION

Figure 1:
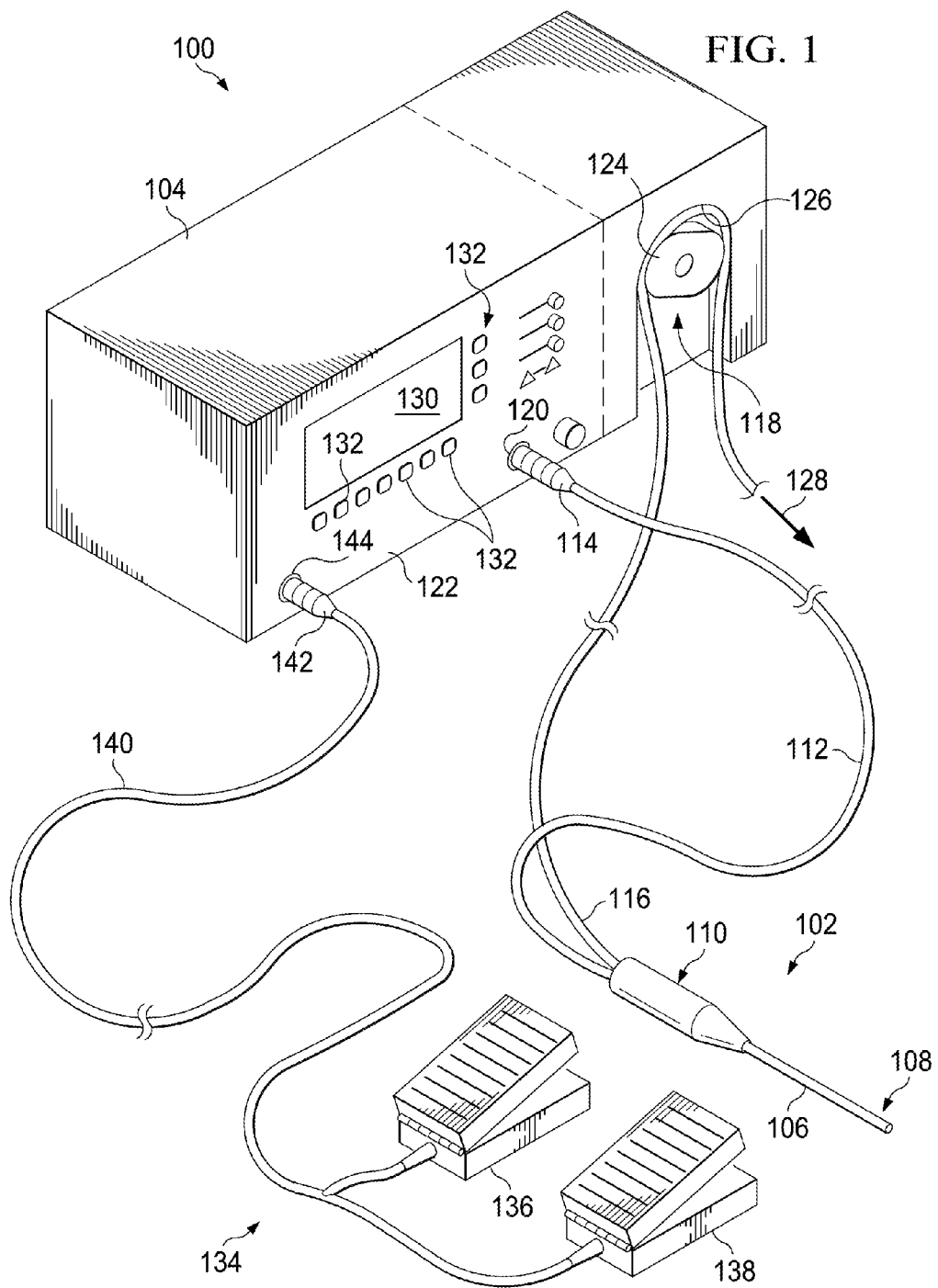
FIG. 1 is a perspective view of an electrosurgical system including an electrosurgical probe and electrosurgical power supply, in accordance with at least some embodiments.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present invention may have a variety of configurations. However, one variation of the device employs a treatment device using Coblation® technology. The assignee of the present invention developed Coblation technology. Coblation technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially nonthermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomenon can be found in commonly assigned U.S. Pat. No. 5,697,882 the complete disclosure of which is incorporated herein by reference.

In some applications of the Coblation technology, high frequency (RF) electrical energy is applied in an electrically conducting media environment to shrink or remove (i.e., resect, cut, or ablate) a tissue structure and to seal transected vessels within the region of the target tissue. Coblation technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomenon can be found in commonly assigned U.S. Pat. Nos. 6,355,032; 6,149,120 and 6,296,136, the complete disclosures of which are incorporated herein by reference.

The active electrode(s) of a Coblation device may be supported within or by an inorganic insulating support positioned near the distal end of the instrument shaft. The return electrode may be located on the instrument shaft, on another instrument or on the external surface of the patient (i.e., a dispersive pad). The proximal end of the instrument (s) will include the appropriate electrical connections for coupling the return electrode(s) and the active electrode(s) to a high frequency power supply, such as an electrosurgical voltage generator.

In one example of a Coblation device for use with the embodiments disclosed herein, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation treatment device for use according to the present embodiments may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often to deliver therapeutic levels of energy where the tissue is treated, between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source may deliver a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly frequencies around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 μH to 50,000 μH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Moreover, other treatment modalities (e.g., laser, chemical, other RF devices, etc.) may be used in the inventive method either in place of the Coblation technology or in addition thereto.

"Active electrode" or "active electrode terminal" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

FIG. 1 illustrates an electrosurgical system 100 in accordance with at least some embodiments. In particular, the electrosurgical system 100 comprises an electrosurgical wand or probe 102 coupled to an electrosurgical controller 104 (hereinafter "controller 104"). The wand 102 comprises an elongate housing or elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads, and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end portion 108 of the wand 102. In accordance with various embodiments, the tubular member 116 couples to a peristaltic pump 118, the pump being illustratively shown as an integral component with the controller 104. In other embodiments, an enclosure for the peristaltic pump 118 may be separate from the enclosure 122 for the controller 104 (as shown by dashed lines in the figure), but in any event the peristaltic pump is operatively coupled to the controller 104. In the context of the various embodiments, the peristaltic pump 118 creates a volume-controlled aspiration from a surgical field at the distal end portion 108 of the wand 102.

Still referring to FIG. 1, a display device or interface device 130 is visible through the enclosure 122 of the controller 104, and in some embodiments a user may select operational modes of the controller 104 by way of the interface device 130 and related buttons 132. In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the operational mode. For example, pedal device 136 may be used for on-off control of the application of radio frequency (RF) energy to the wand 102. Further, pedal device 138 may be used to control and/or set the mode of ablation of the electrosurgical system. In certain embodiments, control of the various operational or performance aspects of controller 104 may be activated by selectively depressing finger buttons located on handle 110 of wand 10 (the finger buttons not specifically shown so as not to unduly complicate the figure).

In example systems the controller 104 may include a voltage generator (not shown) for generating an alternating current (AC) that is coupled to wand 102. Controller 104 may also have a processor (not shown) disposed within enclosure 122. The processor may be a microcontroller from any of a variety of available sources, such as one of the many microcontrollers available from Freescale Semiconductors, Inc. of Austin, Tex. The processor may have onboard non-volatile memory within which various programs and data may be stored. In example systems, the non-volatile memory may store a program that, when executed by the processor, causes the processor to periodically read various electrical parameter or temperature measurement sensors (not shown) electrically coupled to the processor and then digitally send the values to the controller 104.

Figure 2:
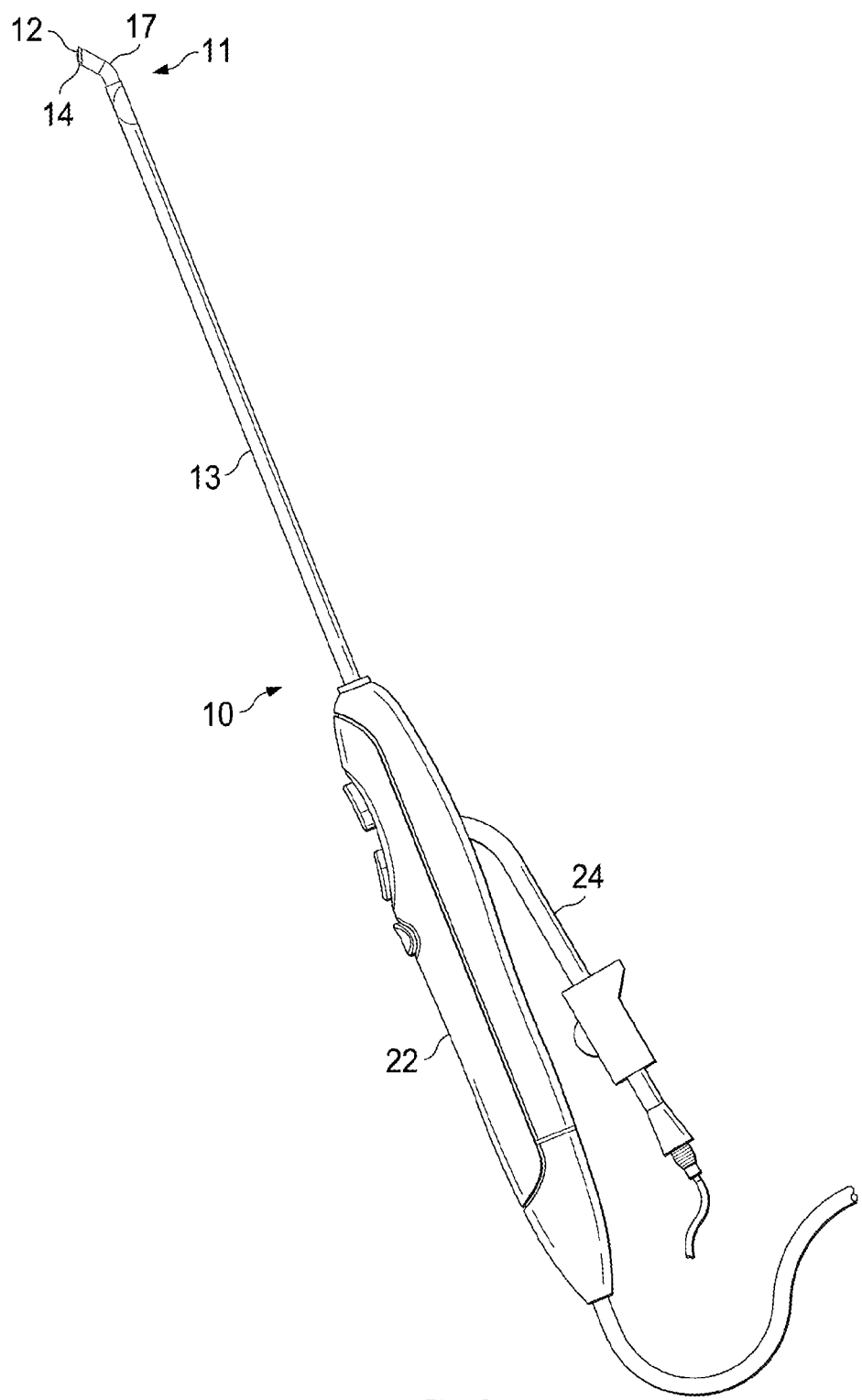
FIG. 2 is side view of an electrosurgical probe according to the present embodiments.

Referring now to FIG. 2, an electrosurgical wand or probe 10 representative of the currently described embodiments includes an elongate shaft 13 which may be flexible or rigid, a handle 22 coupled to the proximal end of shaft 13 and an electrode support member 14 coupled to the distal end of shaft 13. Probe distal portion 11 includes an active electrode or active electrode terminal 12 disposed on the distal tip of shaft 13, support member 14 and a return electrode 17. Active electrode terminal 12 may be connected to an active or passive control network within a power supply and controller 104 (see FIG. 1) by means of one or more insulated electrical connectors (not shown in FIG. 2). The active electrode 12 is electrically isolated from a common or return electrode 17 which is disposed on the shaft proximally of the active electrode 12, preferably being within 1 mm to 25 mm of the distal tip. Proximally from the distal tip, the return electrode 17 is generally concentric with the shaft of the probe 10. The support member 14 is positioned distal to the return electrode 17 and may be composed of an electrically insulating material such as epoxy, plastic, ceramic, glass or the like. Support member 14 extends from the distal end of shaft 13 (usually about 1 mm to 20 mm) and provides support for active electrode 12.

Probe 10 may further include at least one fluid lumen for aspirating excess fluids, bubbles, tissue fragments, and/or products of ablation from the target site and/or delivering electrically conductive fluid. A lumen (not shown here) may extend from the active electrode 12 through shaft 13 and handle 22 to an external connector 24 for coupling to a flexible fluid tube (such as exemplary fluid tube 116 shown in FIG. 1). In the case of aspiration, a vacuum source is a standard hospital pump that provides suction pressure to connector 24.

Figure 3:
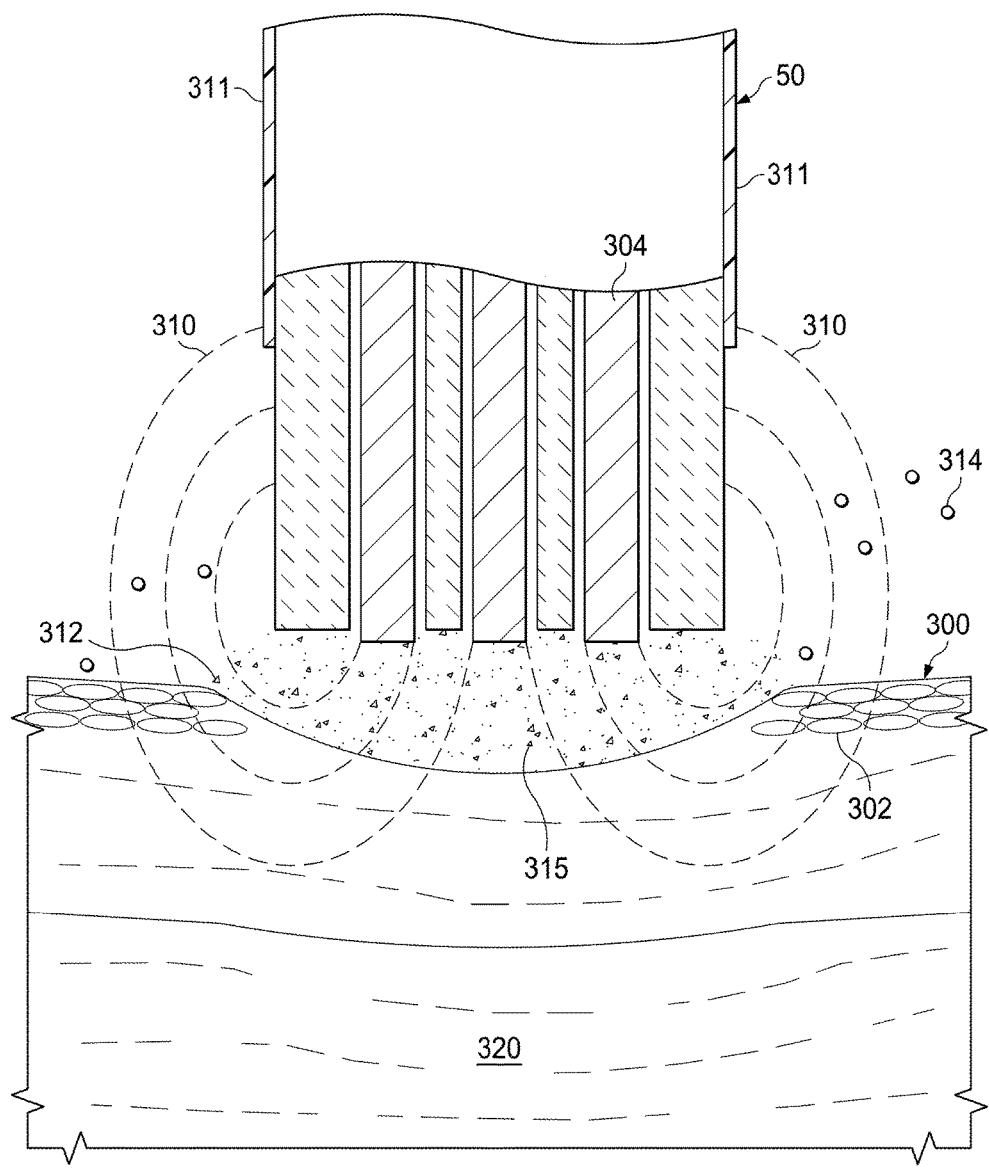
FIG. 3 illustrates a detailed view illustrating ablation of tissue, in accordance with at least some embodiments.

FIG. 3 representatively illustrates in more detail the removal of a target tissue by use of an embodiment of a representative electrosurgical probe 50 according to the present disclosure. As shown, the high frequency voltage is sufficient to convert the electrically conductive fluid (not shown) between the target tissue 302 and active electrode terminal(s) 304 into an ionized vapor layer 312 or plasma. As a result of the applied voltage difference between electrode terminal(s) 304 and the target tissue 302 (i.e., the voltage gradient across the plasma layer 312), charged particles 315 in the plasma are accelerated. At sufficiently high voltage differences, these charged particles 315 gain sufficient energy to cause dissociation of the molecular bonds within tissue structures in contact with the plasma field. This molecular dissociation is accompanied by the volumetric removal (i.e., ablative sublimation) of tissue and the production of low molecular weight gases 314, such as oxygen, nitrogen, carbon dioxide, hydrogen and methane. The short range of the accelerated charged particles 315 within the tissue confines the molecular dissociation process to the surface layer to minimize damage and necrosis to the underlying tissue 320.

During the process, the gases 314 may be aspirated through a suction opening and suction lumen to a vacuum source (not shown). In addition, excess electrically conductive fluid, and other fluids (e.g., blood) will be aspirated from the target site 300 to facilitate the surgeon's view. During ablation of the tissue, the residual heat generated by the current flux lines 310 (typically less than 150° C.) between electrode terminals 304 and return electrode 311 will usually be sufficient to coagulate any severed blood vessels at the site. If not, the surgeon may switch the power supply (not shown) into the coagulation mode by lowering the voltage to a level below the threshold for fluid vaporization, as discussed above. This simultaneous hemostasis results in less bleeding and facilitates the surgeon's ability to perform the procedure.

Figure 4A:
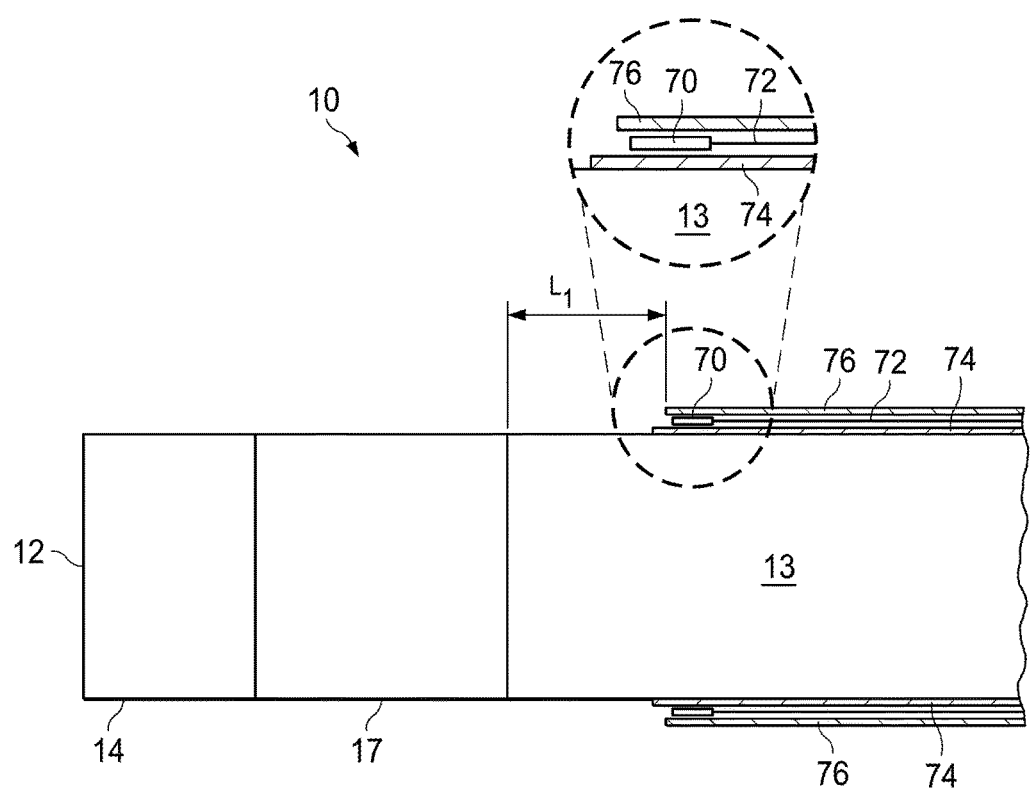
FIG. 4A is a partial cross-sectional side view of a temperature sensor positioned along the shaft of an electrosurgical probe, proximal of an electrode assembly, in accordance with at least some embodiments.

Because of the energy generated and applied during treatment within the patient body with the above-described probe or other variations thereof, the actual temperature of any electrically conductive fluid irrigating the treated body space, joint, or tissue region may generally increase with energy application. Accordingly, probe 10 may include mechanisms for measuring a temperature of the electrically conductive fluid itself without being overly influenced by the surgical effect occurring at the active electrode 12. Turning to FIG. 4A, one embodiment is illustrated in the side view of probe 10 and the detail side view showing a temperature sensor 70 positioned along the probe shaft proximally of the return electrode 17. Temperature sensor 70 may comprise any number of sensors, e.g., thermocouple, thermistor, resistance temperature detector (RTD), etc. In particular, temperature sensor 70 may comprise a T-type thermocouple as these sensors are well-established for use in such probes.

To reduce or eliminate the temperature-monitoring influence from an active electrode 12 during tissue treatment, sensor 70 is desirably distanced from both the active electrode 12 and return electrode 17 and may accordingly be positioned proximally along the shaft 13 of probe 10. In the example shown, the distance $L_1$ of sensor 70 removed from return electrode 17 is at least 5 mm but may also be less than or greater than this distance, as practicable. With sensor 70 positioned accordingly, the sensor 70 may measure the temperature of the infused electrically conductive fluid/irrigant or any medium surrounding the probe 10 and sensor 70 as the temperature of the fluid is indicative of the temperature of the surrounding tissue or joint space within which probe 10 may be positioned for treatment. The fluid temperature may thus be measured without regard to any energy generated by the current traveling between active electrode 12 and return electrode 17 of probe 10.

Temperature sensor 70 may be mounted directly upon the shaft as illustrated in FIG. 4A. However, certain embodiments of probe 10 may have a suction lumen (not shown here) for aspirating fluid and ablative byproducts from the treatment site, wherein the inflow and/or outflow of fluid and gas through the underlying suction lumen may affect the temperature sensed by sensor 70. Thus, a thermally insulative layer 74 such as heat shrink tubing or other insulation (e.g., comprised of thermoplastics, such as polyolefin, polyvinyl chloride (PVC), polytetrafluoroethylene (PTFE), fluorinated ethylene propylene (FEP), etc.) may be placed between the temperature sensor 70 and outer surface of shaft 13. Sensor 70 may be secured directly to the shaft 13 and/or underlying layer 74 via another insulative layer 76 overlying sensor 70 and conducting wire 72 coupled to sensor 70. This overlying insulative layer prevents the temperature of the surrounding fluid from effecting the measurement at sensor 70. The addition of the overlying layer 76, which may be comprised of any of the materials mentioned above, may also electrically isolate temperature sensor 70 from its surrounding saline environment to prevent or inhibit electrical noise from being introduced into the temperature measurement circuit. Overlying layer 76 may be adhesive lined to further isolate the sensor 70.

Figure 4B:
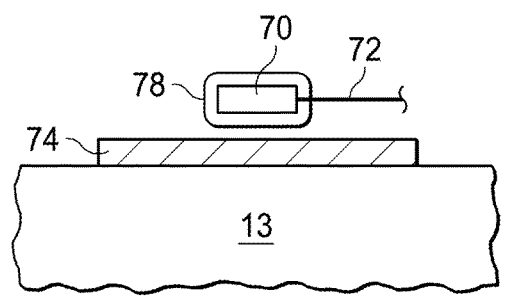
FIG. 4B is a detail cross-sectional side view of a temperature sensor insulated via an adhesive, in accordance with at least some embodiments.

Additionally and/or alternatively, temperature sensor 70 may be isolated and secured to the underlying layer 74 by an adhesive 78, e.g., epoxy or cyanoacrylate glue, which may be adhered directly upon sensor 70, as illustrated in the detail side view of FIG. 4B.

In another embodiment, not shown here but described in U.S. patent application Ser. No. 12/771,129, filed on Apr. 30, 2010 entitled "Electrosurgical Systems and Method having Enhanced Temperature Measurement," the complete disclosure of which is herein incorporated by reference, includes a variation where multiple temperature sensors 70, e.g., greater than one sensor, may be positioned around the shaft 13 to obtain multiple readings of the fluid temperature. Multiple temperature sensors 70 may be uniformly positioned relative to one another about a circumference of shaft 13, or they may be alternatively positioned at arbitrary locations as well. In sensing the multiple fluid temperatures, each of the temperatures may be displayed to the user and/or alternatively they may be calculated to present an average temperature value to the user and/or the maximum of the measured values may be displayed.

Figure 5:
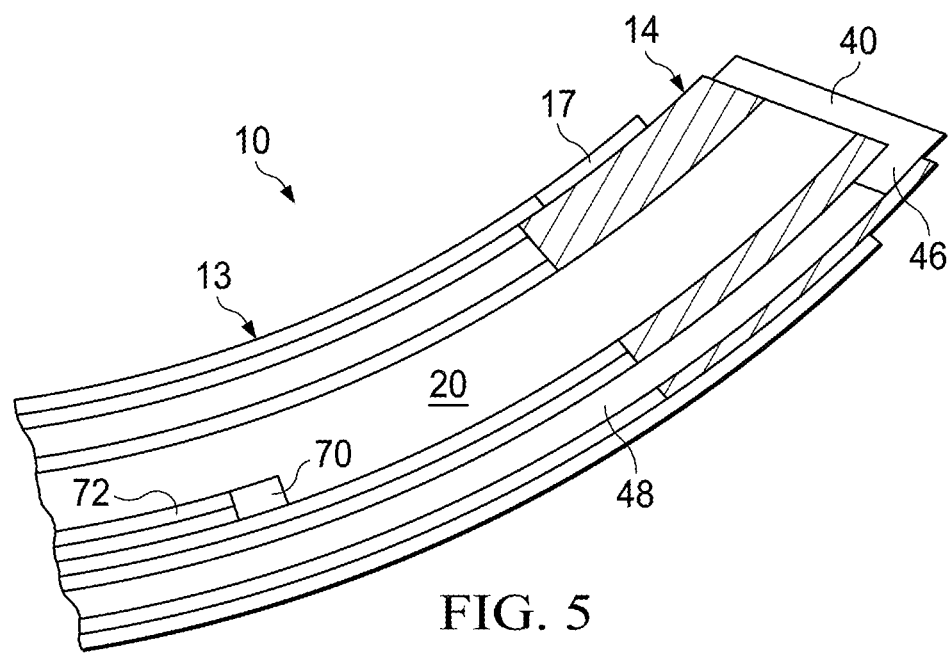
FIG. 5 is a side view of another embodiment of a temperature sensor that may be positioned within a fluid lumen of an electrosurgical probe to sense the fluid temperature immediately removed from the vicinity of the active electrode, in accordance with at least some embodiments.

Referring now to FIG. 5, in yet another variation a representative probe 10 having a suction lumen 20 for aspirating electrically conductive fluid from the body or joint space, a temperature sensor 70 and conducting wire 72 may be alternatively positioned within the suction lumen 20 itself, as illustrated in the detail cross-sectional view of FIG. 5. In this example, a temperature of the electrically conductive fluid recently in the immediate vicinity of the active screen electrode 40 and then aspirated into suction lumen 20 may be measured as one method for determining a temperature-effect induced in nearby tissues due to the electrosurgical procedure. Such temperature measurements could be used to control the RF output in order to provide therapies where it may be desirable to elevate the temperature of the target tissue to a specific temperature range. This configuration may also yield temperature data that may be used to directly correlate the temperature of the target tissue from the aspirated conductive fluid/irrigant and thereby allow the user to get direct feedback of the actual temperature of the tissue and/or limit the RF output depending on preset limits or for a given procedure or tissue type.

Independently from or in addition to the temperature sensing mechanisms in or along the probe 10, the power supply/controller 104 may also be configured for determining and/or controlling a current output. The current output during normal therapeutic operation is typically in the range of about 200 mAmps (mA) or less, with an approximate 300V (RMS) voltage, as discussed earlier. Means for sensing current output are described in U.S. Pat. No. 6,235,020, filed Apr. 10, 1998, entitled "Power Supply and Methods for Fluid Delivery in Electrosurgery" the complete disclosure of which is herein incorporated by reference. As discussed previously, when a probe 10 is in close proximity to a metallic object or electrically conductive object such as another surgical instrument or scope, a less than optimal situation may occur and power supplied to probe 10 may be diverted and create an arc between the active electrode (s) and metallic object. This may damage the metallic instrument and also damage the active electrode surface, potentially altering the tissue effect preferentially created by the active electrode. According to certain embodiments described herein, the controller 104 may therefore be programmed to perform a pre-test in a lower voltage mode, lower voltage pulse or check mode for a period of time, before returning to a standard operating mode for delivering a higher therapeutic voltage level to the target tissue.

This lower voltage mode may be performed at any time before delivering a therapeutic voltage level to the tissue, either upon initial activation whereby the user commands the controller to deliver power by depressing a foot pedal or hand switch for example, or periodically throughout the duration of a procedure during suspensions in the periods of delivery of therapeutic voltage associated with standard operational use of the probe. This check mode may also be performed automatically after any arc has been detected and before returning to therapeutic voltage levels without the input command from the user to the system 100 being altered, i.e. the user may not disengage or deactivate the foot pedal or the finger switch. The lower voltage delivered during the pre-test or check mode may range between 10-90 VRMS, chosen so as to minimally alter the surrounding tissue and minimally affect any temperature signals during this testing period, and is sent to the probe for a relatively short duration (i.e., for less than approximately 100 ms). More preferably, the lower voltage delivered during the pre-test or check mode is in the range of 30-60 VRMS.

The current measured during the lower voltage mode is compared to predetermined high and low current limits, which may be set based on several variables discussed below in more detail. If the measured current falls outside of the specified limits, the higher voltage delivery levels appropriate for normal therapeutic operation are not allowed to activate. The current measurement may continue until the user deactivates the probe, or until the current measurement falls within the specified high and low threshold values corresponding to the relevant operational variables. Current measurement may also be programmed to repeatedly occur periodically over the duration of the probe's procedural use.

When electrodes are immersed in an electrically conductive medium, an electrode circuit may be formed. This electrode circuit includes the plasma created in operational relationship to the active electrode of the probe, the electrically conductive fluid between the active and return electrodes, and the electrode-medium interface. As a result of this configuration, the electrode circuit has or presents a certain amount of impedance to the flow of energy away from the active electrode toward a return electrode. The impedance presented by the electrode circuit may be dependent on many factors. In particular, this electrode circuit impedance between the two electrodes may be the sum of: 1) the electrode/medium interface for each electrode (i.e., active electrode(s) and return electrode(s)); and, 2) the impedance of the medium between the two electrodes. As to the first factor, the impedance of the electrode interface with the medium is a function of the electrode electrical properties, affected by the electrode surface area in contact with the medium, as well as the quality of the electrode surface. In this application, the quality of the electrode surface is primarily affected by the wear of the electrode surface material after an amount of elapsed duration of use. As to the second factor, the impedance of the medium between the electrodes (return and active) is a function of the electrical conductivity of the medium (or whatever material is located between the electrodes, such as tissue) and the distance between the electrodes. In the case of electrically conductive fluids such as saline selected as the medium, this impedance alters with changes to the temperature of the medium. Therefore the inventors of the present disclosure have discovered that the minimum current (or maximum electrode circuit impedance) that may result in an arc to a nearby metallic object varies depending on many variables, including but not limited to the distance between the active electrode and a metallic instrument, the style of the probe (e.g. the active electrode size and shape and tip angle), the wear on the active electrode associated with the elapsed duration of use of the probe, and the temperature adjacent the active electrode or in an electrically conductive fluid or medium surrounding the probe. For example, the high threshold current limit measured in the lower voltage check mode may be set so that when the probe is close to a metallic instrument (and thus the system may be susceptible to generating an undesirable current arc) the measured current is expected to exceed the prescribed high threshold current limit, and the system would therefore prevent activation of the higher voltage delivery levels appropriate for normal therapeutic operation. Similarly, by way of example the low threshold current limit may be set so that when a probe is not surrounded by irrigating fluid (such as saline typically used in an arthroscopic joint capsule) the current measured is expected to be lower than the prescribed low threshold current limit, so that the system does not activate the normal therapeutic higher voltage delivery level under such conditions.

Figure 6:
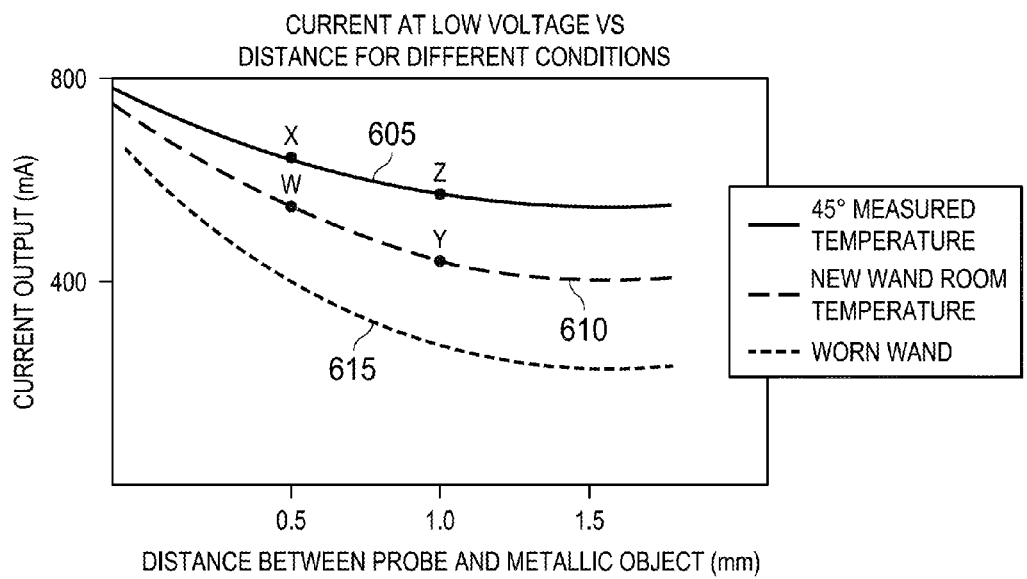
FIG. 6 is an illustrative graph comparing current at low voltage versus distance from a metallic object for differing probe conditions, in accordance with at least some embodiments.

FIG. 6 shows an exemplary chart illustrating how the current output at which an arc occurs varies with distance between a probe active electrode and metallic object for differing probe conditions. In general, when a large metallic object such as a retractor, endoscope or implant is placed in an electrically conductive fluid near an active and return electrode, that metallic object will have a similar potential to the return electrode. Therefore, the electrode circuit impedance of a system may generally be altered should a metallic instrument be disposed at a distance similar to or less than the separation between a probe's active and return electrode. Accordingly, as shown in FIG. 6, the current output at the initial low voltage delivery will increase as the distance or separation of the large metallic object from the probe's electrodes is reduced. The curve depicted in FIG. 6 may be used to set the high current limit based on an expected maximum distance between the large metallic object and the probe's electrodes at which an arc tends to occur. FIG. 6 shows an exemplary current output curve 605 for a newly activated wand at the low voltage signal used for the initial measurement when the surrounding conductive fluid in measured at a temperature of 45° C., typically indicative of the temperature of an irrigating fluid present in a joint capsule after an elapsed period of ablation during an electrosurgical procedure. FIG. 6 also shows an exemplary curve for an output current 610 with a new wand the low voltage signal used for the initial measurement when the temperature of the surrounding medium is measured closer to room temperature (e.g., 25° C.), such as when the probe is first activated in the joint capsule, or in some instances where the probe may be inadvertently activated outside of the irrigating fluid-infused arthroscopic surgical field. FIG. 6 also shows an exemplary third curve for an output current 615 for a wand with substantial electrode wear due to significant elapsed duration of use of the probe, at the low voltage signal used for the initial measurement when the conductive fluid is measured at approximately 25° C. As shown, the arcing current output values measured vary depending on the distance the metallic object is from a probe, as well as on the wear on a probe active electrode, and the temperature of the medium sensed adjacent the active electrode. The wear on a probe active electrode, or the condition of the active electrode after an elapsed duration of use, may be determined by several measured and processed electrical parameters, such as energy dissipated by the system across the active electrode, duration of energy delivery across the active electrode, and type of usage of the system (i.e., delivery ablation or coagulation voltage levels).

For example, at a distance of 0.5 mm, where arcing is likely to occur when therapeutic voltage levels are delivered, a probe disposed in a medium at 25° C., indicated by point W, may produce a current output at the low voltage signal used for the initial measurement of approximately 550 mA, versus a new probe at typical operating temperatures (45° C.), indicated by point X on curve 605, which may produce a current output at the low voltage signal used for the initial measurement of approximately 680 mA. Therefore the controller 104 may be programmed to initially pulse the power output at approximately 50 VRMS in the lower voltage mode for a period of time or for a suspension period and concurrently measure the current output. If the current output is above a certain upper current output limit, such as 550 mA at 25° C. or 680 mA at 45° C., then the controller may not permit a therapeutic level of voltage (approximately 300 VRMS) to be delivered until the current drops below this current output upper limit. This current output upper limit may be defined by a combination of a set of preprogrammed values, encoded within the controller 104 (based on probe type, or procedure for example), that are then further refined or modified based on measured values such as temperature measurements from a sensor disposed near the active electrode and/or methods that involve ascertaining electrode wear such as measurement of the energy dissipated by the system across a given electrode, the number of activations, or the total time of activation. For example, certain procedures use more coagulation voltages that generate more heat, affecting the measured output current significantly.

Looking at a second example at a separation or distance of 1.0 mm between the large metallic object and the probe, a probe disposed in a medium at 25° C., indicated by point Y, may produce a current output at the low voltage signal used for the initial measurement of approximately 450 mA, versus a new probe at typical operating temperatures (45° C.), indicated by point Z on curve 605, that may produce a current output at the low voltage signal used for the initial measurement of approximately 600 mA for this given probe style. Therefore, if the probe is new or little worn, and the temperature of the surrounding medium has been measured around 45° C., the controller 104 may reference point Z on the curve 605, and the new limiting value may be higher at approximately 600 mA compared with a cooler temperature, which may have a limiting value of 400 mA to 450 mA. As a further refinement, the inventors further envisage that the number of activations or length of activation of a wand may also be quantified, and a worn wand with lower measured surrounding temperatures may have an even lower high current threshold closer to approximately 300 mA. As shown in FIG. 6 and described earlier, an increase in temperature of the medium acts so as to increase the measured current output threshold limit, as elevated temperatures in the electrically conductive medium tend to reduce the impedance of the conductive medium. If temperature is not taken into account, then a higher measured current output threshold limit could easily be interpreted as a false indication of the potential for arcing, or a faulty instrument, and not just an effect of the localized temperature, which may prevent activation of the higher voltage delivery levels appropriate for normal therapeutic operation and be potentially be frustrating to the user.

Figure 7:
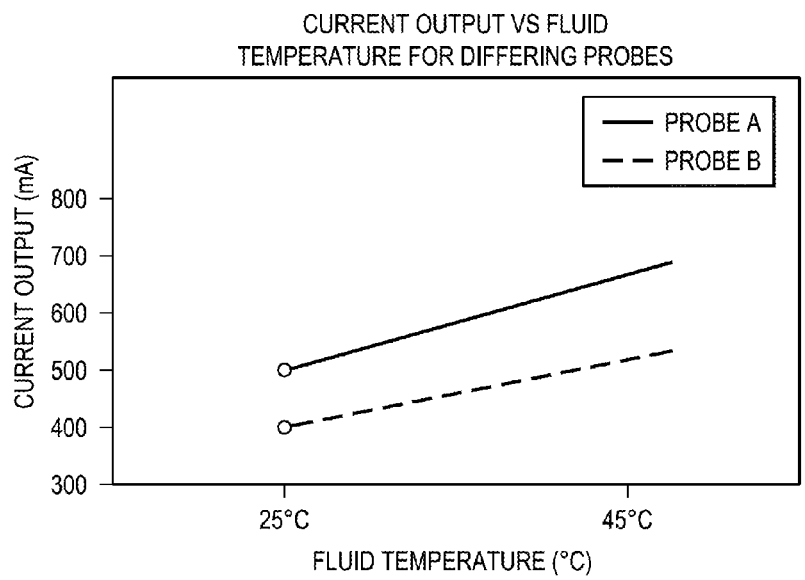
FIG. 7 is an illustrative graph comparing current output with fluid temperature changes for different probe types, in accordance with at least some embodiments.

Shown in FIG. 7, an exemplary chart shows the current output measured versus fluid temperature, for two exemplary probes (probe A and probe B) differing in active electrode shapes, sizes and tip angles. This data was taken at an exemplary lower voltage of 50 VRMS. As discussed earlier, the impedance of an electrically conductive medium generally decreases in a logarithmic manner as temperatures increase; therefore, elevated conductive fluid temperatures will result in lower electrode circuit impedance and therefore an increase in the measured current output. Therefore the controller may be preprogrammed to account for the probe type and to use the measured temperature to refine or modify an upper limit for the current output threshold limit. For example, for probe A in warmer sensed temperatures, a high current threshold or limit may approximate 650 milliamps (mA), whereas for probe B, in cooler temperatures, a high current threshold may approximate 400 mA. In certain embodiments, the controller 104 may be programmed to generate an alarm or indication to the user, should these high current threshold limits be exceeded for a certain period of time. In other variations, the controller may be programmed to automatically shut off the power completely.

The low voltage mode may last in a range between 5 ms and 50 ms. It is preferable for the period to minimally impact the user, so as to not feel like a delay in activation, however current and temperature readings need sufficient time to normalize, especially if the low voltage mode occurs immediately after a therapeutic or higher voltage mode. It has been found that a minimum period of time between 5 ms and 50 ms may be preferable. The period of time is preferably sufficient for any electrically noise to diminish, and for the temperature measurement of the surrounding medium to stabilize. In one embodiment, the suspension period is set at a constant value equal to or greater than 100 ms, and more preferably equal to or greater than 250 ms. After this minimum suspension period, the cycle may be repeated leading to serially incremental suspension periods at the lower voltage mode. Alternatively, after the minimum suspensions period, the lower voltage mode may extend continuously, until the current output reaches an acceptable level, or a maximum time value has been reached, when further feedback may be indicated to the user. In alternative embodiments, the controller 104 may permit the suspension period to continue until the temperature varies less than about 1 degree Celsius per 50 ms.

In other variations, the controller 104 may also be programmed with a low current limit threshold (or a high impedance limit) with appropriate alarms or indications to the user. Low current limit threshold measurements may occur due to insufficient electrically conductive fluid adjacent the active and return electrodes, or a fault in the probe. This low current threshold measurement may also be detected during the check mode or low voltage mode.

Figure 8:
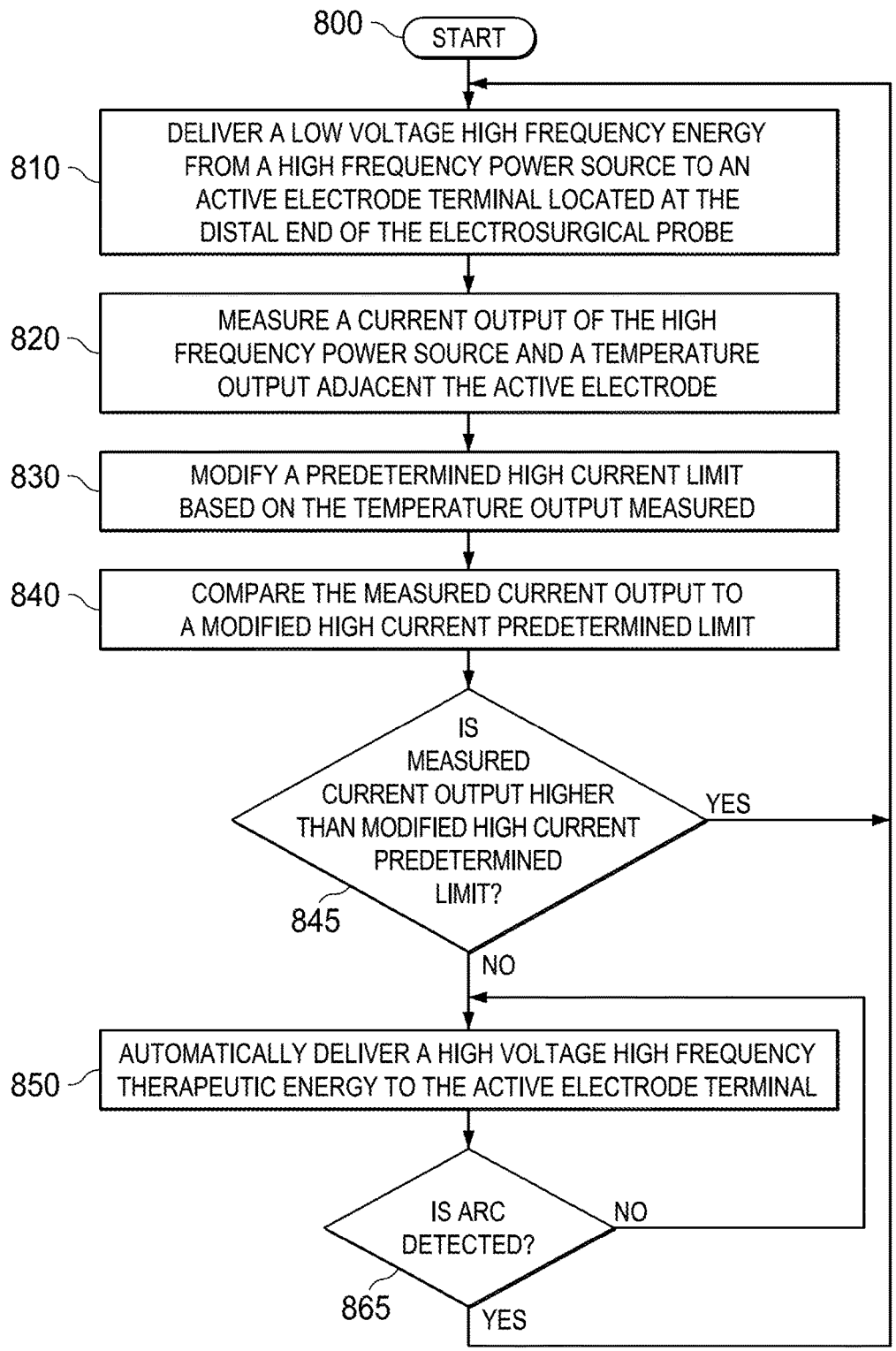
FIG. 8 is a flow chart representing a method to reduce arcing during an electrosurgical procedure, in accordance with at least some embodiments.

FIG. 8 shows a controller flowchart for enhanced reduction of arcing from an electrosurgical probe to an adjacent metallic implement, in accordance with at least some embodiments. In particular, the method starts (block 800) and proceeds to: delivering a low voltage high frequency energy from a high frequency power source to an active electrode terminal located at the distal end of the electrosurgical probe (810), followed by measuring a current output of the high frequency power source and a temperature output adjacent the active electrode (820), followed by modifying or adjusting a preprogrammed high current limit, encoded within the controller based on the temperature output (830); and then comparing the measured current output to this now modified high current predetermined limit (840). If the current output is below the modified predetermined limit, the controller may continue to the step of automatically delivering a high voltage high frequency therapeutic energy to the active electrode terminal (850). If the current output is above the modified predetermined limit, the controller may repeat the steps of delivering low voltage energy (810), sensing and measuring the current output and temperature (820), modifying the preprogrammed high current limit based on the temperature output (830); and then comparing the measured current output to a modified high current predetermined limit (840). If while delivering the high voltage therapeutic energy (850) an arc is detected the controller may automatically return to the steps of delivering low voltage energy 810, sensing and measuring the current output and temperature 820, modifying the preprogrammed high current limit based on the temperature output (830); and then comparing the measured current output to a modified high current predetermined limit (840). All steps listed above may occur automatically.

In an alternative embodiment, the method described above may first include commanding a controller to deliver a therapeutic level of energy to an active electrode disposed at a distal end of an electrosurgical instrument, and a therapeutic energy may be delivered at the outset, up until an arc is detected or a user commands the controller to halt delivery. While therapeutic energy is being delivered, if an arc is detected, the controller may then automatically indicate this fault to the user and may simultaneously or at approximately the same time, reduce the high frequency energy to a low voltage mode delivered to the active electrode terminal. While in this low voltage mode, the controller may then perform the steps of measuring the current output of the high frequency power source and a temperature output adjacent the active electrode, followed by modifying or adjusting a preprogrammed high current limit, encoded within the controller based on the temperature output; and then comparing the measured current output to this modified high current preprogrammed determined limit. The controller may perform these steps of measuring, modifying and comparing once the temperature measurements have stabilized, which may be at least 10 ms-50 ms. The controller may then return to the therapeutic mode if the current output is below this modified predetermined limit. In other variations, the controller may also compare the measured current output to a low current preprogrammed limit also, to detect high impedance faults such as damaged instruments or a lack of sufficient electrically conductive fluid. The controller may also only return to the therapeutic mode if the current output is above the preprogrammed lower current limit.

Other modifications and variations can be made to the disclosed embodiments without departing from the subject invention. For example, other uses or applications are possible. Similarly, numerous other methods of controlling or characterizing instruments or otherwise treating tissue using electrosurgical probes will be apparent to the skilled artisan. Moreover, the instruments and methods described herein may be utilized in instruments for various regions of the body (e.g., shoulder, knee, etc.) and for other tissue treatment procedures (e.g., chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical system for treating tissue comprising:
    an electrosurgical probe comprising a shaft having a distal end and a proximal end, an active electrode disposed near the distal end;
    a high frequency power supply for delivery of high frequency voltage to said active electrode, the high frequency power supply coupled to the active electrode and a return electrode;
    a controller electrically connected to receive and process a signal from a current sensor, the current sensor operable to measure a current output associated with the power supply when a low voltage output is delivered to the active electrode or the return electrode; and
    wherein the controller is programmed to prevent delivery of a therapeutic voltage output, until the current signal received is within a range, said range having adjustable limits and wherein the controller is further programmed to adjust said limits based on at least one measured value, the measured value indicative of active electrode wear or electrical conductivity of an electrically conductive fluid adjacent the active electrode.

2. The system of claim 1, wherein the controller is electrically connected to receive and process a signal from a temperature sensor, wherein the temperature sensor is disposed in the electrically conductive fluid.

3. The system of claim 2, wherein the at least one measured value comprises temperature.

4. The system of claim 3 wherein the range defines an upper current limit that is adjusted so as to increase as the temperature increases.

5. The system of claim 2, wherein the at least one measured value comprises temperature measured from the temperature sensor; the measured temperature indicative of the electrically conductivity of the electrically conductive fluid.

6. The system of claim 1, wherein the controller is operable to automatically adjust the power supply to the therapeutic voltage output if the current output is within the range.

7. The system of claim 6, wherein the controller is operable to automatically interrupt the power supply from delivering the therapeutic voltage output if the current output is outside the range.

8. The system of claim 7 wherein the controller is operable to deliver the low voltage output for at least one suspension period, and then return to the therapeutic voltage output if the current output is within the range.

9. The system of claim 8 wherein the suspension period is at least 5 ms.

10. The system of claim 1 wherein the range has a lower limit operable to detect high electrode circuit impedance faults in the probe or insufficient electrically conductive fluid adjacent the active and return electrode.

11. The system of claim 1 wherein the at least one measured value comprises a total length of time the probe has been delivering therapeutic energy.

12. The system of claim 1 wherein the controller is configured to identify a device type of said electrosurgical probe when operationally connected to the high frequency power supply and to automatically determine the range specific to the device type.

13. An electrosurgical method for minimizing arcing between an electrosurgical probe and a metallic object comprising:
delivering a low voltage from a power source to an active electrode or a return electrode of the electrosurgical probe;
sensing a current output of the power source adjacent to the active electrode or the return electrode of the electrosurgical probe;
modifying a predetermined high current limit based on at least one measured value indicative of conductivity of an electrically conductive fluid present adjacent the active or return electrode;
comparing the sensed current output to the modified high current predetermined limit; and
preventing the delivery of a therapeutic voltage output until the sensed current output is less than the modified predetermined high current limit.

14. The method of claim 13 further comprising the step of automatically delivering the therapeutic energy if the sensed current output is below the modified predetermined limit.

15. The method of claim 14 wherein said delivering the therapeutic energy forms a plasma in the vicinity of the active electrode.

16. The method of claim 14 further comprising automatically repeating the steps of delivering, sensing, modifying and comparing, should an arc be detected between the active electrode and a metallic object while delivering the therapeutic energy.

17. The method of claim 13 comprising repeating the step of delivering low voltage energy for at least one suspension period, and then returning to delivering the therapeutic energy if the sensed current output is below the modified predetermined limit.

18. The method of claim 13 wherein the steps of delivering, sensing, modifying and comparing lasts at least 5 ms.

19. The method of claim 13 wherein the active electrode is positioned in electrically conductive fluid during the procedure and wherein a current flow path from the active electrode, through the electrically conductive fluid, to the return electrode is created when the voltage is delivered.

20. The method of claim 13, further comprising sensing a fluid temperature adjacent the distal end of the electrosurgical probe.

21. The method of claim 20, wherein the at least one measured value comprises the fluid temperature.

22. The method of claim 21 wherein increases in the fluid temperature modifies the predetermined high current limit so as to increase said limit.

23. The method of claim 13 further comprising comparing the measured current output to a low current predetermined limit, operable to detect high impedance faults and wherein the steps of delivering, sensing and comparing are repeated if the measured current output is below the low current predetermined limit.

24. The method of claim 13 wherein the low voltage is sufficiently low so as to not affect any adjacent tissue.

25. An electrosurgical system for treating tissue at a target site comprising:
an electrosurgical probe comprising a shaft having a distal end and a proximal end, an active electrode disposed near the distal end;
a power supply for delivery of a voltage to said active electrode, the power supply coupled to the active electrode and a return electrode;
a controller operable to receive a signal from a current sensor and a temperature sensor, the current sensor operable to measure the current output of the power supply and the temperature sensor configured to send a signal indicative of a temperature of electrically conductive fluid adjacent the active electrode; and
wherein the controller is programmed to automatically suspend delivery of a therapeutic level of energy to the active electrode for at least one suspension period, and wherein the controller is operable to deliver a low voltage output during the at least one suspension period while measuring the current output and the receiving a signal indicative of temperature, and wherein the controller is operable to automatically deliver the therapeutic level of energy once the suspension period is complete and once the current output drops below an upper limit, wherein the upper limit is an adjustable limit, adjusted based on the temperature signal.

26. An electrosurgical system comprising:
a processor;
a memory coupled to the processor;
a voltage generator communicatively coupled to the processor;
a temperature sensor communicatively coupled to the processor;
wherein the memory stores a program that, when executed by the processor, causes the processor to:

receive a value indicative of a current output associated with the voltage generator during periods of time when a low voltage output is being delivered to an active electrode of an electrosurgical probe;

determine at least one output current range limit, indicative of the presence of a metallic object within a distance from the active electrode of the electrosurgical wand by:

monitoring at least one measured value indicative of at least one condition selected from the group consisting of: wear of the active electrode, and a temperature associated with an fluid in the vicinity of the active electrode, modifying the at least one current output range limit based on the measured value; and prevent delivery of a therapeutic voltage output until the current output is within modified current range.

27. The system of claim 26 wherein when the processor determines, the program causes the processor to adjust an upper limit of the range based on the temperature associated with the fluid in the vicinity of the active electrode.

28. The system of claim 26 wherein when the processor determines, the program causes the processor to adjust an upper limit of the range based on the active electrode condition of the electrosurgical wand.

* * * * *